US009131906B2

(12) United States Patent
Hoornaert

(10) Patent No.: US 9,131,906 B2
(45) Date of Patent: Sep. 15, 2015

(54) METHOD FOR SIMULATING REDUCTION OF ACQUISITION DOSAGE OF AN X-RAY SYSTEM, COMPUTER SYSTEM AND X-RAY SYSTEM

(75) Inventor: Bart Pierre Antoine Jozef Hoornaert, Arendonk (BE)

(73) Assignee: Koninklijke Philips N.V., Eindhoven (NL)

( * ) Notice: Subject to any disclaimer, the term of this patent is extended or adjusted under 35 U.S.C. 154(b) by 96 days.

(21) Appl. No.: 13/518,906

(22) PCT Filed: Dec. 23, 2010

(86) PCT No.: PCT/IB2010/056042
§ 371 (c)(1),
(2), (4) Date: Jun. 25, 2012

(87) PCT Pub. No.: WO2011/083388
PCT Pub. Date: Jul. 14, 2011

(65) Prior Publication Data
US 2012/0263367 A1    Oct. 18, 2012

(30) Foreign Application Priority Data
Jan. 6, 2010    (EP) .................................... 10150170

(51) Int. Cl.
*G06K 9/00*    (2006.01)
*A61B 6/03*    (2006.01)
(Continued)

(52) U.S. Cl.
CPC . *A61B 6/032* (2013.01); *A61B 6/06* (2013.01); *A61B 6/488* (2013.01); *A61B 6/504* (2013.01); *A61B 6/542* (2013.01); *A61B 6/502* (2013.01)

(58) Field of Classification Search
None
See application file for complete search history.

(56) References Cited

U.S. PATENT DOCUMENTS 6,829,323 B2    12/2004    Toth et al.
6,904,162 B2 *    6/2005    Robar et al. .................. 382/128
(Continued)

FOREIGN PATENT DOCUMENTS

WO    2007114470 A1    10/2007

OTHER PUBLICATIONS

P. Massoumzadeh et al., "Noise Simulation in X-Ray CT", Proceedings of SPIE, vol. 5745, May 13, 2005, pp. 898-909.

*Primary Examiner* — Nancy Bitar

(57) ABSTRACT

The present invention relates to X-ray generating technology in general. It is desirable to perform an X-ray image acquisition with a minimal required dosage for obtaining a desired image quality. Accordingly, a method for simulating reduction of acquisition dosage of an X-ray image, a computer system, an X-ray system, a computer-readable medium and a program element is provided. The method (30) for simulating reduction of acquisition dosage of an X-ray system comprises providing (32) first X-ray image information comprising first noise, the first X-ray image information having been acquired with a first dosage setting; providing (34) a second dosage setting; determining (36) a noise difference for obtaining simulated second X-ray image information acquired with the second dosage setting and applying (38) the noise difference to the first X-ray image information for obtaining the simulated second X-ray image information comprising second noise. The noise difference is at least partly dependent on at least one of a coloring of the first noise, a noise power spectra of the first noise, a coloring of the noise difference, a power spectra of the noise difference, an intensity distribution of the first X-ray image information and a local intensity distribution of the first X-ray image information.

20 Claims, 3 Drawing Sheets

(51) Int. Cl.
*A61B 6/06* (2006.01)
*A61B 6/00* (2006.01)

(56) References Cited

U.S. PATENT DOCUMENTS

| | | | |
|---|---|---|---|
| 7,480,365 B1 | 1/2009 | Topfer et al. | |
| 8,055,039 B2 * | 11/2011 | Wu et al. | 382/128 |
| 8,270,560 B2 * | 9/2012 | Hirokawa et al. | 378/4 |
| 8,310,567 B2 * | 11/2012 | Kim et al. | 348/242 |
| 8,571,639 B2 * | 10/2013 | Mostafavi | 600/428 |
| 2004/0017880 A1 * | 1/2004 | Toth et al. | 378/4 |
| 2005/0008115 A1 * | 1/2005 | Tsukagoshi | 378/4 |
| 2006/0274877 A1 | 12/2006 | Noshi et al. | |
| 2007/0189455 A1 * | 8/2007 | Allison | 378/95 |
| 2009/0041193 A1 * | 2/2009 | Topfer et al. | 378/108 |
| 2010/0091950 A1 * | 4/2010 | Ellinwood et al. | 378/97 |

* cited by examiner

METHOD FOR SIMULATING REDUCTION OF ACQUISITION DOSAGE OF AN X-RAY SYSTEM, COMPUTER SYSTEM AND X-RAY SYSTEM

TECHNICAL FIELD OF THE INVENTION

The present invention relates to X-ray generating technology in general. More particularly, it relates to a method for simulating reduction of acquisition dosage of an X-ray system, a computer system, an X-ray system, a computer-readable medium and a program element. In particular, the present invention relates to the simulation of a reduction in acquisition dosage of an X-ray system which is dependent on one of noise colour, noise power spectra and an intensity distribution.

BACKGROUND OF THE INVENTION

Regularly, acquired X-ray image information is displayed to a person, e.g. an operator, employing post-processing functionality like adjustability of contrast, brightness and sharpness of the X-ray image information for providing a personalized, preferred look for the depiction of X-ray image information. This may be the case e.g. in medical imaging applications, security imaging applications or inspection imaging applications. According post-processing functionality may only alter the way X-ray image information is displayed without actually changing acquisition parameters like e.g. a certain dosage setting resulting in a patient dose. Especially in medical imaging applications the ALARA (as low as reasonably achievable) requirement must be met while maintaining an image quality and thus patient dose to allow acquisition of X-ray image information with sufficient detail to allow evaluating X-ray image information with regard to the intended application.

E.g. in case of medical imaging applications, a clinical user may have a set of acquired X-ray images, e.g. of patients. The X-ray images may be acquired directly from an X-ray imaging apparatus, e.g. a CT system, or may be stored in an image database on a storage element being previously acquired. The images may be stored as raw images, i.e. as they have been acquired, without any further post-processing. When displaying acquired X-ray images on a display element to the operator, there may be limited post-processing functionality available for varying the look and feel of the acquired image information like adjusting contrast, brightness and/or sharpness, possibly at the cost of more noise within the picture. However, this kind of post-processing functionality may not alter image information itself, e.g. the intrinsic signal-to-noise ratio of the acquired image information, but merely changes the look, thus keeping the intrinsic signal-to-noise ratio (SNR) unaltered. Known post-processing functionality may not allow an operator to estimate a priori e.g. how much image quality of an X-ray image would be degraded in case the dosage setting for acquiring X-ray images would be reduced.

Accordingly, it may be beneficial to determine, in particular simulate, image quality of an X-ray image as a function of applied dosage of X-radiation.

SUMMARY OF THE INVENTION

Thus, there may be a need to provide means for simulating an X-ray image, which would have been acquired employing a certain dosage from acquired X-ray image information.

Consequently, a method for simulating reduction of acquisition dosage of an X-ray image, a computer system for simulating reduction of acquisition dosage of an X-ray image, an X-ray system, a computer-readable medium as well as a program element according to the independent claims are provided.

According to an exemplary embodiment of the present invention, a method for simulating reduction of acquisition dosage of an X-ray image comprises providing first X-ray image information comprising first noise, the first X-ray image information having been acquired with a first dosage setting, providing a second dosage setting, determining a noise difference for obtaining simulated second X-ray image information acquired with the second dosage setting and applying the noise difference to the first X-ray image information for obtaining the simulated second X-ray image information comprising second noise, wherein the noise difference is at least partly dependent on at least one of a colouring of the first noise, a noise power spectra of the first noise, a colouring of the noise difference, a power spectra of the noise difference, an intensity distribution of the first X-ray image information and a local intensity distribution of the first X-ray image information.

According to a further exemplary embodiment of the present invention, a computer system for simulating reduction of acquisition dosage of an X-ray image is provided, comprising a processing element, wherein the processing element is adapted to carry out the method according to the present invention.

According to a further exemplary embodiment of the present invention, an X-ray system is provided, comprising an X-ray generating device, an X-ray detector and a computer system according to the present invention; wherein an X-ray object is arrangeable between the X-ray generating device and the X-ray detector and wherein the X-ray generating device and the X-ray detector are operatively coupled such that X-ray image information of the object is obtainable.

According to a further exemplary embodiment of the present invention, a computer-readable medium is provided, comprising program code, which program code is adapted, when being executed by a processing element, to carry out the method according to the present invention.

According to a further exemplary embodiment of the present invention, a program element is provided, comprising a program, which program is adapted, when being executed by a processing element, to carry out the method according to the present invention.

One aspect of the present invention may be seen as providing means for generating an X-ray image, having a dosage setting, from an actual acquired X-ray image having a different, for example higher, dosage setting. E.g. a drop in X-radiation dosage may be simulated so that an operator is enabled to determine image quality of an X-ray image of an object to be examined, e.g. a patient, having a certain exposure or X-radiation dosage without actually being required to acquire X-ray image information with an X-ray system being set to the desired dosage. Thus, X-ray image information may be acquired with a high X-radiation dosage with a subsequent simulated reduction of exposure or X-radiation dosage resulting in the display of a simulated X-ray image comprising the so reduced dosage for determining and/or comparing image quality versus dosage setting.

With regard to the ALARA requirement, a minimal dosage setting may be determined, which would still provide X-ray image information having an image quality sufficient for e.g. a diagnostic evaluation. Thus, a reduced dosage setting may not be required to be acquired by employing trial and error, e.g. by acquiring X-ray images with a reduced dosage setting, possibly resulting in an X-ray image having an image quality too poor for a certain diagnostic purpose. Also, acquiring multiple individual X-ray images comprising individual dosage settings may be cumbersome, time-consuming and possibly hazardous to living tissue. It may be achievable to balance image quality, with regard to a signal-to-noise ratio of the image information versus exposure or patient dose.

The method according to the present invention may be applied to X-ray image information obtained from an X-ray system e.g. by a recent, current image acquisition procedure or may employ patient information and X-ray image information stored e.g. on a storage element in a database. By employing previously acquired X-ray image information, e.g. from the storage element, a desired minimal exposure or X-radiation dosage with regard to a desired image quality may be based on a certain patient population with regard to a specific clinical task, e.g. fluoro image acquisition versus exposure or brain versus kidney image acquisition or may be patient type specific e.g. adults versus pediatrics.

Thus, the present invention allows an operator to simulate a dose reduction. The operator may interactively enter a new dose, which shall be applied to an X-ray image, e.g. a newly acquired or stored image, or even several images of a dedicated patient or several images of different patients however for the same clinical application, with a simulated X-radiation image being generated, e.g. in accordance with a corrected signal-to-noise ratio for the dose to be simulated. With regard to a graphical user interface, an operator may employ a patient dose reduction slider while an X-ray image of that set dosage setting is displayed on e.g. a monitor. The operator may thus determine image quality while varying the dosage setting of the X-ray image information in an interactive, real-time way.

The signal-to-noise ratio may be reduced by adding noise to the X-ray image information. Preferably, not only the amount of added noise but also the noise colour of the noise to be added may be taken into account. An according determined dosage setting still providing sufficient image quality for a desired application may be stored and may be employed e.g. for future image acquisition applications.

A reduction in signal-to-noise ratio of an X-ray image may thus take into account a certain noise colour and/or an intensity distribution, in particular a local intensity distribution, of the X-ray image e.g. with the respect of the surface of an X-ray detector.

The noise colour may in particular be understood as noise with a frequency dependent footprint. For example, quantum noise may comprise a low pass structure, e.g. pink noise, which falls off at −3 dB per doubling of the frequency, or brown noise, which falls off with −6 dB per doubling of the frequency. Electronic noise may be of a white noise shape, possibly being frequency independent. For flat X-ray detectors, the colour of the noise may be also dependent on the detection technique, e.g. a scintillator having a low pass shape or direct detection having a frequency independent or white shape. An X-ray detector may even comprise different noise colours horizontally versus vertically. Thus, an X-ray detector dependent noise colour may be applied.

The exact shape of the coloured noise however may also be dosage-dependent. Accordingly, when simulating a different dosage, a noise difference, possibly a frequency dependent noise difference may be employed over a mere reduction of the signal-to-noise ratio. However, a signal-to-noise ratio is one example of a noise difference.

The amount of noise or the variance, i.e. the volume of the noise power spectra, may also be dependent on a certain dosage setting or detector dose in nGy and the signal height or signal amplitude, e.g. having an intensity distribution or a local intensity with regard to the surface of the X-ray detector and the individual X-ray detector element pixels respectively.

In real clinical images, all grey levels of an acquired X-ray image may be considered to actually correspond to a different detector dose being applied to the respective pixel element of the X-ray image detector. Therefore, noise variance may be considered to be varying in a well-defined way over the image. Thus, since each grey level corresponds to a distinct detector dose, the respective noise colour or noise power spectra associated with the detector dose may be different. Thus, when considering an intensity distribution or a local intensity of an X-ray image may be understood as employing a dose-dependent noise colour or a dose-dependent noise power spectra, in particular locally dose-dependent with regard to an individual X-ray detector element pixel.

E.g., a clinical X-ray image, which is set to correspond to 100 nGy, may be considered to actually comprise an average signal, in a certain measuring field, which corresponds to an average noise level, which could have been measured with a homogeneous phantom beforehand. In reality, a darker part of an image, which has a signal, which is e.g. ten times lower than average, may be considered to have only received 10 nGy locally. Therefore, a location dependent, locally varying noise variance linked to the respective local detector dose level may be present. In particular, every pixel of an X-ray detector may be considered to comprise a different, individual grey level, which may then correspond to its own detector dosage and according noise, in particular noise colour.

When employing a Variance Stabilization Transform, an image may be obtainable in which the noise variance becomes signal independent. For quantum limited X-ray images, the Variance Stabilization Transform may be approximated by applying a square-root gray level transform. This may be implemented e.g. via a Look-Up-Table.

Now artificial noise with a suitable frequency dependency, also referred to as "colour"), may be required to be added. When only quantum noise needs to be added, the colour of the noise power spectrum may depend on different factors, such as the detector technology, e.g. indirect detection with a scintillator, or direct conversion, detector design e.g. scintillator thickness and read-out design, detector manufacturing process with regard to isotropic noise power spectrum, and other factors related to e.g. scaling and/or binning. In case further noise sources, e.g. electronic noise and/or structure noise, may become relevant, they may have to be modelled as well, and finally the combined noise amplitude with the combined colour may has to be modelled and added. An inverse transform with regard to the noise variance as indicated above, may result in an image with noise added, which may not only comprise a preferred noise colour and may also fulfill the required relation between noise variance and signal height due to the previously performed transform prior to adding coloured noise. Standard post-processing of an X-ray system may now continue.

In other words, X-ray image information is first transformed to arrive at X-ray image information having a dose independent noise variance. Subsequently coloured noise having a suitable noise colour is added. Furthermore, an inverse transform of the X-ray image information with added noise is performed.

An intensity distribution or a local intensity of X-ray image information may also be understood as having a dose distribution or a local dose with respect to the detector element pixels.

In the following, further embodiments of the present invention are described referring in particular to a method for simulating reduction of acquisition dosage of an X-ray image, a computer system for simulating reduction of acquisition dosage of an X-ray image, an X-ray system, a computer-readable medium and a program element. However, it is to be understood that the explanations provided apply to all of the different entities described herein. Accordingly, arbitrary variations and interchanges of single or multiple features between the claimed entities is conceivable and within the scope and disclosure of the present patent application.

According to a further exemplary embodiment of the present invention, the noise difference may be a local noise difference, in particular dependent on the local intensity distribution of the first X-ray image information.

A local noise difference may allow providing a dose dependent colour of the noise or signal-to-noise ratio, in particular locally. The relevant dose may the dose of X-radiation arriving at the individual X-ray detector element pixels.

According to a further exemplary embodiment of the present invention, the first X-ray image information may comprise a first signal-to-noise ratio. The method may further comprise, in particular instead of the steps associated to a noise difference, determining a second signal-to-noise ratio from the second dosage setting and determining the noise difference for obtaining the simulated second X-ray image information comprising the second signal-to-noise ratio. The second signal-to-noise ratio may at least be partly dependent on at least one of the colouring of the first noise, the noise power spectra of the first noise, the colouring of the noise difference, the power spectra of the noise difference, the intensity distribution of the X-ray image information and the local intensity of the first X-ray image information.

A signal-to-noise ratio may be interpreted as an example for a noise difference.

According to a further exemplary embodiment of the present invention, the method may further comprise displaying at least the simulated second X-ray image information, wherein the second dosage setting is changeable and wherein the simulated second X-ray image information is displayed substantially simultaneous to a change of the second dosage setting.

Accordingly, an operator may be allowed to interactively determine a minimum dosage setting while maintaining a desired image quality by real-time inspection of the simulated second X-ray image information.

According to a further exemplary embodiment of the present invention, the first noise may be smaller than the second noise and/or the first signal-to-noise ratio may be larger than the second signal-to-noise ratio. The noise difference may be noise to be added. Accordingly, noise may be added additionally to noise already present within the first X-ray image information to increase the overall noise thus reducing the second signal-to-noise ratio.

According to a further exemplary embodiment of the present invention, the computer system may comprise a storage element, an input element and a display element. The storage element may be adapted for providing X-ray image information, the input element may be adapted for receiving a second dosage setting, and particular input by an operator, and the display element may be adapted for displaying at least one of first X-ray image information and simulated second X-ray image information.

The computer system may be adapted to allow an interactive evaluation of minimum dosage e.g. from stored patient data within a database on the storage element. An operator may employ the input element, e.g. a slider, knob, switch, keyboard or touch screen control for inputting a desired second dosage setting with the display element subsequently displaying at least the simulated second X-ray information for providing a visual feedback regarding the image quality of an X-ray image employing a second dosage setting.

According to a further exemplary embodiment of the present invention, the first X-ray image information may be provided by an X-ray system.

Here, X-ray image information may have been acquired recently by an X-ray system from an object to be examined, e.g. a patient for determining a second dosage setting for an e.g. subsequent image acquisition procedure.

According to a further exemplary embodiment of the present invention, the computer system may be adapted for displaying simulated second X-ray information substantially in real-time when changing the second dosage setting.

According to a further exemplary embodiment of the present invention, the computer system may be adapted for providing image post processing prior to displaying X-ray image information, with the image post-processing being in particular dependent at least in part on the X-ray image information to be displayed.

Without X-ray image information dependent post-processing, at least with regard to the simulated second X-ray image information, e.g. contrast may not be maximized due to e.g. a difference or shift in dynamic range of the first X-ray image information and the simulated second X-ray image information. Accordingly, image post-processing may in particular be dependent on the actual X-ray image information to be displayed.

According to a further exemplary embodiment of the present invention, the computer system may be couplable with an X-ray system and may be adapted to control the X-ray system.

Accordingly, it may be beneficial for an operator to control not only the display of X-ray image but also control the acquisition procedure from an X-ray system. Possibly even a remote storage system for providing previously acquired X-ray image information of multiple patients from a patient's database may be conceivable.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

Figures are not drawn to scale, however may depict qualitative proportions.

DETAILED DESCRIPTION OF EMBODIMENTS

Figure 1:
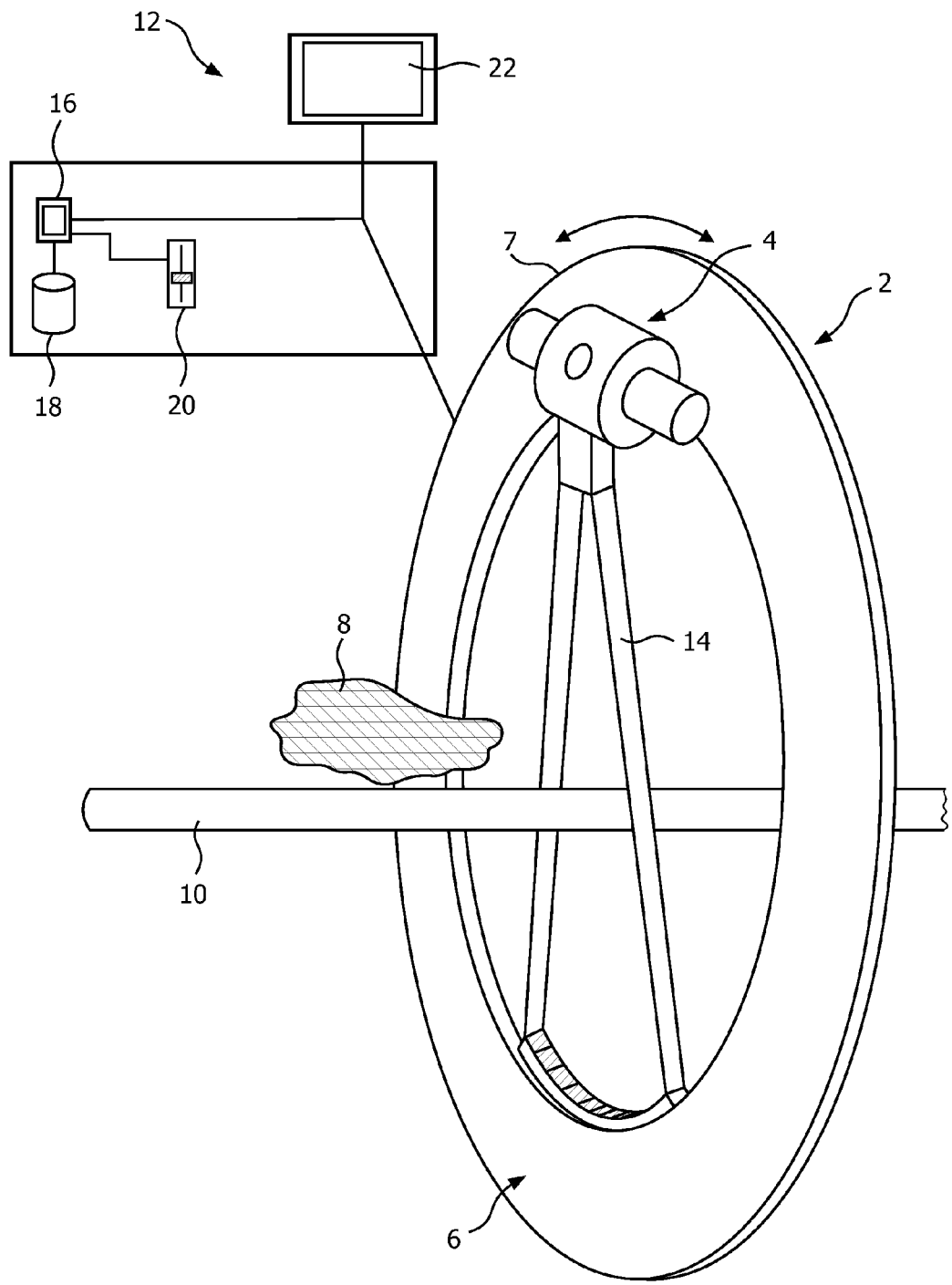
FIG. 1 shows an exemplary embodiment of an X-ray system, comprising a computer system, according to the present invention.

Now referring to FIG. 1, an exemplary embodiment of an X-ray system comprising a computer system, according to the present invention is depicted.

In FIG. 1, an X-ray system 2 comprising an X-ray generating device 4 and an X-ray detector 6, is depicted. X-ray detector 6 is exemplary depicted as a line array, however a two-dimensional curved or flat image detector is conceivable as well. X-ray generating device 4 is emanating X-radiation 14 in a direction of X-ray detector 6.

Situated on a support 10, object 8 is arranged, possibly arrangeable in the path of X-radiation 14 between X-ray generating device 4 and X-ray detector 6. Both the X-ray generating device 4 and the X-ray detector 6 are mounted on a rotatable gantry 7 for rotation about the object 8. Connected to the X-ray system 2 is computer system 12 for controlling acquisition parameters of the X-ray system 2 as well as evaluating and/or storing acquired X-ray image information by X-ray system 2.

Computer system 12 comprises a processing element 16 to which a storage element 18 is connected to. Storage element 18 may be adapted for providing program information to processing element 16 as well as storing image information acquired from X-ray system 2 and/or possibly further logical image acquisition systems located remotely, e.g. throughout a medical facility. An input element 20, in FIG. 1 depicted exemplary as a slider, is arranged at computer system 2 for providing a dosage setting, e.g. for a subsequent image acquisition procedure, to computer system 12 or for controlling or inputting further parameters e.g. a dosage setting for a simulation of a reduction of acquisition dosage. A display element 22 is arranged at computer system 12 for display of X-ray image information and/or further acquisition relevant information.

E.g., an X-ray image of object 8 may be acquired by X-ray system 2 and being subsequently displayed on display element 22 of computer system 12. The acquired image may comprise a defined dosage. Input element 20 may be employed for inputting a new, desired dosage setting to processing element 16 and computer system 12, respectively, which input is employed by computer system 12 for determining simulated X-ray image information comprising the desired dosage setting input by input element 20, subsequently displaying simulated X-ray image information on display element 22, e.g. for a comparison of image quality of the simulated X-ray image information versus acquired X-ray image information by an operator.

Figure 2:
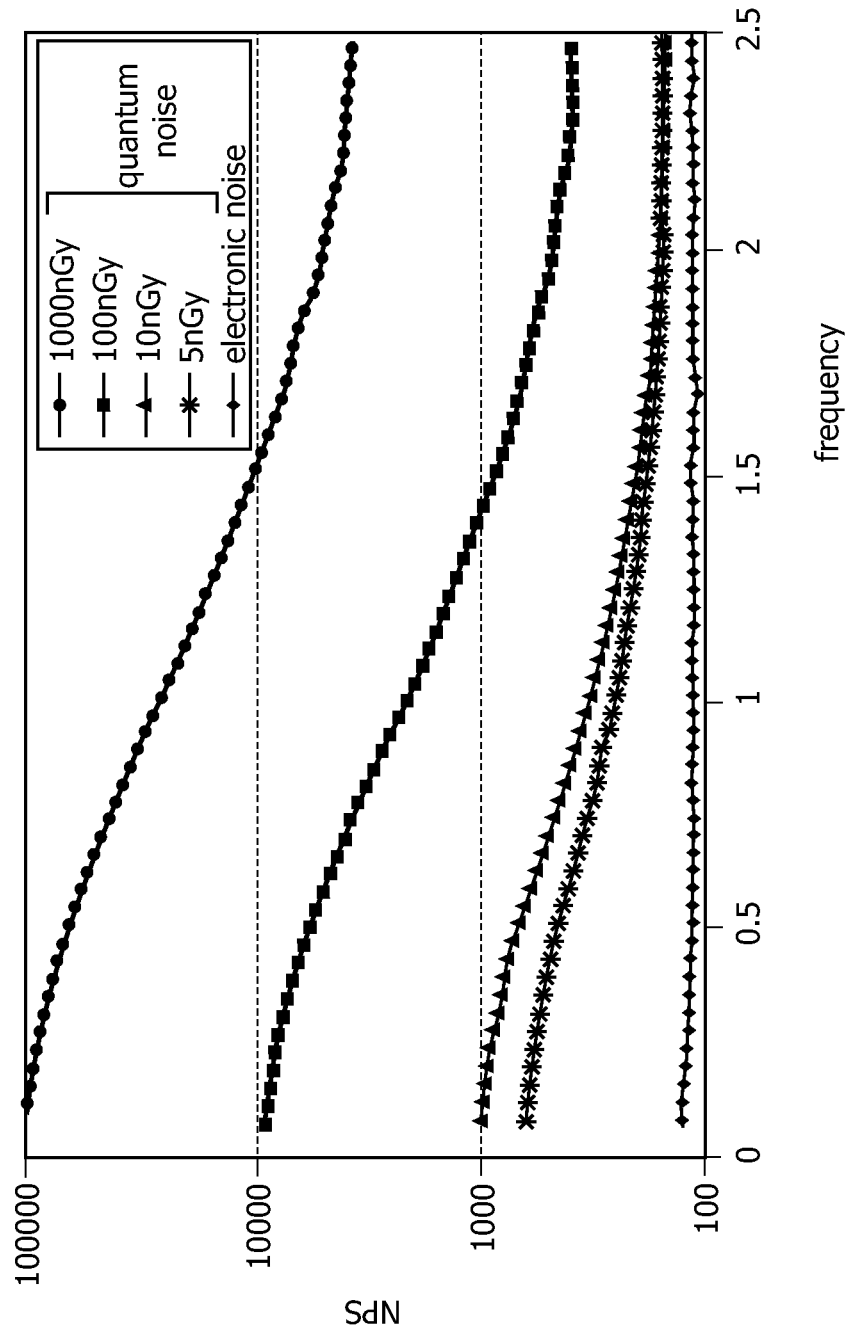
FIG. 2 shows an exemplary embodiment of dose related noise power spectra.

Now referring to FIG. 2, an exemplary embodiment of dose related noise power spectra is depicted.

In FIG. 2, exemplary four individual exposure levels or dosages are depicted. As may be taken from FIG. 2, corresponding noise colour, i.e. the frequency dependency of the noise power spectra, may not be considered substantially equal for all four dosages, which would require the curves to be only shifted in parallel. Rather, also the curvature of the individual frequency dependency of the noise power spectra is altered. Thus, FIG. 2 shows that the noise power spectra with respect to noise colour for a 1.000 nGy dosage is different than the noise colour of e.g. a dosage of 5 nGy. Electronic noise may be considered to be substantially frequency independent, thus comprising a noise colour of white. Thus, detector dose and quantum noise may be considered to be strongly related.

Figure 3:
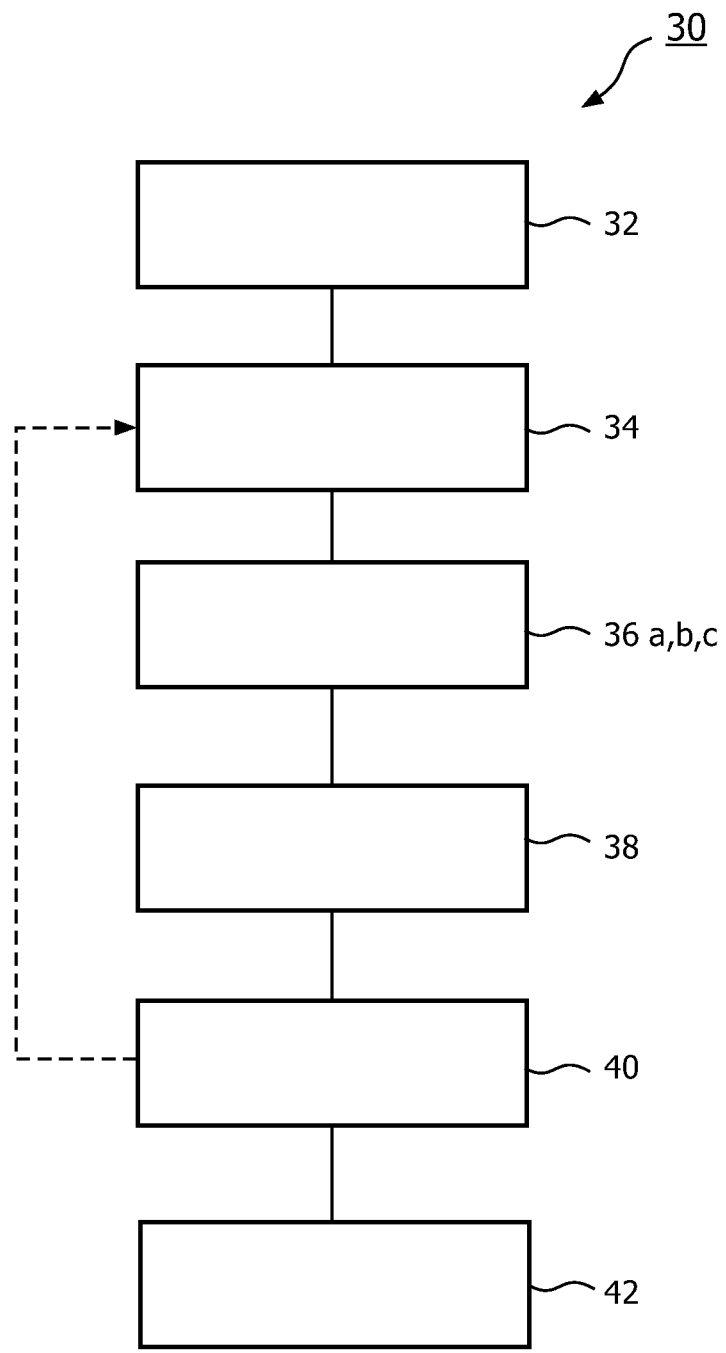
FIG. 3 shows an exemplary embodiment of a method for simulating reduction of acquisition dosage of an X-ray system according to the present invention.

Now referring to FIG. 3, an exemplary embodiment of a method for simulating reduction of acquisition dosage of an X-ray system according to the present invention is depicted.

FIG. 3 shows the method 30 for simulating acquisition dosage reduction comprising providing 32 first X-ray image information comprising first noise, the first X-ray image information having been acquired with a first dosage setting. In this step an operator may either select e.g. previously acquired X-ray image information of patients or may acquire an X-ray image directly from X-ray system 2. The operator may intend to determine a suitable minimal dosage for a required image quality for a specific clinical task. Differences in clinical tasks may e.g. comprise fluoroscopy versus radiography, adults versus pediatrics, brain scan versus kidney scan.

The operator may provide 34 a second dosage setting to a computer system. E.g., the user may vary, in particular reduce, a dosage setting to obtain the preferred second dosage setting, possibly employing a user interface control knob or input element 20.

Furthermore, a noise difference is determined 36 for obtaining simulated second X-ray image information acquired with the second dosage setting. The simulated second X-ray image information is actually not acquired but rather calculated to reflect X-ray image information as it would have been acquired employing the second dosage setting. The noise difference may in particular be the signal-to-noise ratio, a local dose dependent noise difference comprising a local dose dependent noise colour. In other words, the computer system 12 may calculate a signal-to-noise ratio reduction linked to the patient dose reduction as input by the operator.

Thus, the operator may alter, in particular reduce, the requested patient dose, e.g. the second dosage setting, while the system substantially shows the X-ray image information employing the second dosage setting in real-time, i.e. showing how the image information would look like in case they were acquired employing the second dosage setting.

Accordingly, the system translates the reduced, second dosage setting, thus a dosage drop, into a signal-to-noise ratio drop. E.g., if the operator would like to halve the patient dose, the square of the signal-to-noise ratio $SNR^2$ may be halved as well, e.g. via reducing the detector dosage, thus the dosage of X-radiation arriving at the individual detector element pixels, by a factor of 2 or in other words by doubling the quantum noise. A further possibility for a reduction in dosage may be achievable by the usage of additional Cu pre-filtering within the X-ray system 2. Cu pre-filtering may be understood as employing a copper (Cu) filter plate in the path of X-radiation 14 before the X-radiation 14 arrives at the object 8 to be examined. An according copper filter plate may halve the patient dose while the square of the signal-to-noise ratio $SNR^2$ may drop less than a factor of 2. When employing this scheme, less quantum noise compared to the first scheme may be required to be added for arriving at a desired dosage reduction. The relative contrast may be determined by the beam quality while the relative noise may be determined by the applied detector dose settings. Beam quality may be understood as a parameter which indicates the effective energy (keV) of the X-ray beam. It may be dependent on the tube voltage exployed and the filter materials applied, e.g. added copper filters. The system may employ individual schemes, e.g. power reduction or employment of copper filters, for keeping the square of the signal-to-noise ratio as high as possible, while achieving the desired second dosage of the second dosage setting.

Subsequently, computer system 12 may determine 36a a noise difference for obtaining simulated second X-ray image information acquired with the second dosage setting and may apply 38 the noise difference to first X-ray image information for obtaining simulated second X-ray image information, comprising second noise. In particular, the noise difference again may have a local dose dependent noise colour, more in particular for each detector element pixel.

When adding noise, multiple parameters have to be taken into account. The amount of quantum noise and electric noise from an X-ray image may be considered to be X-ray detector dependent. The amount of quantum noise power may only inversely be related to the applied detector dosage. An according parameter may be stored with each image. The amount of quantum noise may beam quality dependent. All relevant beam quality related parameters may be stored with each image in an X-ray system e.g. a cardiovascular system, thus the amount of noise may be known within great accuracy. Either theoretical calculation or a calibration with system specific measurements may be employed to implement the a priori knowledge regarding quality dependent quantum noise.

The electronic noise may be considered to be stable. For detector dose settings regularly employed, electronic noise may be considered to be neglectable.

The amount of quantum noise is also signal dependent, in particular signal intensity dependent. For each distinct intensity, thus local detector dosage, an individual noise amplitude may be required, e.g. by employing the variance stabilization transform. As an approximation, the quantum noise amplitude may be considered to relate to the square root of the signal amplitude.

An example is provided for a cardiovascular X-ray system providing cardiovascular X-ray images.

As a first step, an intensity transform may be required to be undone, which may have been applied to an image stored, for example in a database in raw file format. E.g. a logarithmic or white compression transform may have been applied to the raw images, which may be required to be undone. A white compression may be considered to provide reduced contrast in highlighted or bright, thus white, areas of a picture. Furthermore, a variance stabilization transform may be applied. One example of this transform may be extracting the square root since noise amplitude of X-ray images may be proportional to the square root of the signal. Now, noise variance may be considered to have become independent of the signal intensities, thus noise with a known amplitude and with a suitable colour, e.g. dependent on the X-ray detector employed, may be added to the image. Afterwards, inverse intensity operations, e.g. the inverse of the variance stability transform and a logarithmic or white compression may be applied.

The colour, thus frequency dependency, of the added noise should be adapted to the noise known from the X-ray detector, e.g. a flat detector of which the colour of quantum noise related noise may be considered to be known. A low pass filter may be employed for colouring noise before adding. Electronic noise may be addressed similarly with regard to its frequency dependency or colour.

Subsequently, at least the simulated second X-ray image information may be displayed 40. Here the computer system 12 may provide post-processing and may subsequently display the simulated X-ray image information to the operator.

Post-processing may either employ similar post-processing as was employed when displaying the first X-ray image information. Here reduction in dosage may considered to be substantially only adding noise. This may e.g. be considered to result in an increase of noise while having the contrast of the first X-ray image information. A manual setting e.g. of contrast for providing a well-balanced X-ray image may be performed by the operator e.g. employing a second input element. However, the manual input of e.g. contrast or manual adjustment of contrast may also be implemented within the computer system 12 so that post-processing is automatically adapted to the simulated second X-ray image information. Thus, the operator may not be required to provide two parameters but only one to the computer system when simulating a dose reduction.

The steps of providing a desired second dosage setting until the display of simulated X-ray image information corresponding to the set dosage setting may be iteratively repeated by the operator until a simulated X-ray image having a suitable image quality is obtained. Subsequently, the system may store new acquisition protocol settings and/or new post-processing settings dependent on the set dosage setting and may apply at least one of an acquisition protocol settings the post-processing settings and the second dosage setting for subsequent image acquisition. An according method and computer system may be implemented in any of an X-ray system, a CT system, a cardiovascular X-ray system or even when employing an X-ray system for security imaging applications and inspection imaging applications.

It should be noted that the term "comprising" does not exclude other elements or steps and that the "a" or "an" does not exclude a plurality. Also, elements described in association with different embodiments may be combined. It should also be noted, that reference numerals in the claims shall not be construed as limiting the scope of the claims.

REFERENCE NUMERALS

2 X-ray system
4 X-ray generating device
6 X-ray detector
7 Gantry
8 Object
10 Support
12 Computer system
14 X-radiation
16 Processing element
18 Storage element
20 Input element
22 Display element
30 Method for simulating reduction of acquisition dosage of an X-ray image
32 STEP: Providing first X-ray image information
34 STEP: Providing a second dosage setting
36$a,b,c$ STEP: Determining a noise difference/signal-to-noise ratio
38 STEP: Applying noise difference
40 STEP: Displaying X-ray image information
42 STEP: Storing dosage setting

The invention claimed is:

1. A method for simulating reduction of acquisition dosage of an X-ray image, comprising:
    providing first X-ray image information comprising first noise, the first X-ray image information having been acquired with a first dosage setting;
    providing a second dosage setting;
    determining a noise difference for obtaining simulated second X-ray image information acquired with the second dosage setting, said noise difference reflecting a dose dependence of a shape of a frequency dependent footprint of noise; and
    applying the noise difference to the first X-ray image information for obtaining the simulated second X-ray image information comprising second noise.

2. An apparatus for simulating reduction of acquisition dosage of an X-ray image, comprising an X-ray-dosage-reduction-simulation processor configured for:
    acquiring, via X-rays with a first dosage setting, first X-ray image information comprising first noise;

determining a noise difference for obtaining simulated second X-ray image information acquired with a second dosage setting, calculation of said noise difference taking into account a dose dependence of a shape of a frequency dependent footprint of noise; and applying the noise difference to the first X-ray image information for obtaining the simulated second X-ray image information comprising second noise.

3. The apparatus according to claim 2, wherein the first X-ray image information comprises a first signal-to-noise ratio; said processor being further configured for:

determining a second signal-to-noise ratio from the second dosage setting; and determining the noise difference for obtaining the simulated second X-ray image information comprising the second signal-to-noise ratio;

wherein the second signal-to-noise ratio is at least partly dependent on at least one of coloring of the first noise, a noise power spectra of the first noise, the coloring of the noise difference, the power spectra of the noise difference, the intensity distribution of the first X-ray image information and the local intensity distribution of the first X-ray image information.

4. The apparatus according to claim 2, further comprising a display, said processor being further configured for displaying, via said display, at least the simulated second X-ray image information, the second dosage setting being changeable, the displayed simulated second X-ray image information being displayed substantially simultaneous to a change of the second dosage setting.

5. The apparatus according to claim 2, further configured such that at least one of the first noise is less than the second noise said second X-ray image information includes and the first signal-to-noise ratio is greater than the second signal-to-noise ratio, and such that the noise difference to be applied is noise to be added.

6. The apparatus according to claim 2, further comprising a storage element, an input element, and a display element, said processor being further configured for:

providing, from said storage element, X-ray image information via said input element, receiving said second dosage setting; and via said display element, displaying at least one of first X-ray image information and simulated second X-ray image information.

7. The apparatus according to claim 6, said processor being configured for displaying, via said display element, simulated second X-ray image information substantially in real-time when changing the second dosage setting.

8. The apparatus according to claim 2, said processor being configured for providing image post processing prior to displaying X-ray image information, said image post processing being dependent at least in part on the X-ray image information to be displayed.

9. The apparatus according to claim 2, further comprising:
a computer system that includes said processor; and
an X-ray system by which said processor performs said acquiring, said computer system being configured couplable with said X-ray system so as to control said X-ray system.

10. The apparatus according to claim 2, further configured such that said second dosage setting is changeable interactively for determining a preferred dosage setting, said processor being further configured for at least one of storing, and employing, the determined preferred dosage setting for subsequent acquisition of X-ray image information.

11. The apparatus of claim 2, further comprising an X-ray system, and a computer system that includes said processor, said X-ray system comprising an X-ray generating device, and an X-ray detector for said acquiring, said apparatus being further configured for said generating device and said detector being operatively coupled such that X-ray image information of an object arranged between them is obtainable.

12. The apparatus of claim 2, said simulated second X-ray image information simulating image information that would be acquired with said second dosage setting.

13. The apparatus of claim 2, said simulated second X-ray image information comprising second noise, said noise difference being a measure of a difference between said first noise and said second noise.

14. The apparatus of claim 13, said determining comprising said calculation.

15. The apparatus of claim 3, said determining a second signal-to-noise ratio comprising calculating a reduction from said first signal-to-noise ratio.

16. A non-transitory computer readable medium for simulating reduction of acquisition dosage of an X-ray image, said medium embodying a program having instructions executable by a processor for performing a plurality of acts, among said plurality there being the acts of:

providing first X-ray image information comprising first noise, the first X-ray image information having been acquired with a first dosage setting;

providing a second dosage setting;

determining a noise difference for obtaining simulated second X-ray image information acquired with the second dosage setting, wherein the noise difference is a local noise difference dependent on the local intensity distribution of the first X-ray image information, calculation of said noise difference taking into account a dose dependence of a shape of a frequency dependent footprint of noise; and applying the noise difference to the first X-ray image information for obtaining the simulated second X-ray image information comprising second noise.

17. The computer readable medium of claim 16, said simulated second X-ray image information simulating image information that would be acquired with said second dosage setting.

18. The computer readable medium of claim 17, said simulated second X-ray image information comprising second noise, said noise difference being a measure of a difference between said first noise and said second noise.

19. The apparatus of claim 2, wherein the noise difference is a local noise difference dependent on a local intensity distribution of the first X-ray image information.

20. The apparatus of claim 2, said determining comprising calculating a reduction from a signal-to-noise ratio.

* * * * *